United States Patent
Baumgart

(10) Patent No.: US 8,265,224 B2
(45) Date of Patent: Sep. 11, 2012

(54) SYSTEM FOR ADJUSTING ANGIOGRAPHIC X-RAY IMAGING PARAMETERS BASED ON IMAGE CONTENT

(75) Inventor: John Baumgart, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 141 days.

(21) Appl. No.: 12/877,129

(22) Filed: Sep. 8, 2010

(65) Prior Publication Data

US 2011/0170662 A1 Jul. 14, 2011

Related U.S. Application Data

(60) Provisional application No. 61/294,170, filed on Jan. 12, 2010.

(51) Int. Cl.
*H05G 1/30* (2006.01)
(52) U.S. Cl. .......................................... 378/95; 378/114
(58) Field of Classification Search .................. 378/95, 378/114, 115
See application file for complete search history.

(56) References Cited

U.S. PATENT DOCUMENTS

| | | | |
|---|---|---|---|
| 4,543,604 A * | 9/1985 | Grosse | 378/98.12 |
| 5,448,614 A * | 9/1995 | Suzuki | 378/115 |
| 5,917,883 A * | 6/1999 | Khutoryansky et al. | 378/95 |
| 6,639,211 B1 * | 10/2003 | Anand et al. | 250/282 |
| 7,496,175 B2 | 2/2009 | Sakaguchi et al. | |
| 2006/0203966 A1 * | 9/2006 | Mollus et al. | 378/150 |
| 2006/0293579 A1 | 12/2006 | Schmitt et al. | |
| 2008/0107233 A1 | 5/2008 | Kabushiki et al. | |
| 2008/0319309 A1 | 12/2008 | Bredno et al. | |

* cited by examiner

*Primary Examiner* — Glen Kao
(74) *Attorney, Agent, or Firm* — Alexander J Burke

(57) ABSTRACT

An Angiographic X-ray imaging system includes a detector for automatically detecting a transition between different phases of contrast enhanced blood flow in vessels of a portion of patient anatomy, in response to pixel luminance content of at least one image of a sequence of acquired images of the portion of patient anatomy. An X-ray imaging device uses the detector and information associating different sets of X-ray imaging device settings with corresponding different phases of contrast enhanced blood flow in vessels for automatically sequentially acquiring images in different phases using different imaging settings, in response to detection of transitions between different phases.

21 Claims, 4 Drawing Sheets

US 8,265,224 B2

SYSTEM FOR ADJUSTING ANGIOGRAPHIC X-RAY IMAGING PARAMETERS BASED ON IMAGE CONTENT

This is a non-provisional application of provisional application Ser. No. 61/294,170 filed 12 Jan. 2010, by J. Baumgart.

FIELD OF THE INVENTION

This invention concerns an Angiographic X-ray imaging system for automatically adaptively acquiring a sequence of images of a portion of patient anatomy in different phases of contrast agent flow in anatomical vessels of a patient, for example.

BACKGROUND OF THE INVENTION

It is desirable in angiographic X-ray image data acquisition to minimize the amount of X-ray dose given to a patient throughout the course of an imaging study. This can be done by reducing the X-ray energy or reducing the frame rate of the acquisition. There are applications for X-ray data that may require a portion of an acquisition to be of higher frame rate or dose than another part. Known systems vary the frame rate during an acquisition by either setting timers or using a manual switch to trigger the change. This requires the user to predict the characteristics of the acquisition before starting it, in the case of using timers, or to incur an additional mammal step, in the case of the switch. However a user may incorrectly predict the characteristics or enter incorrect settings for imaging based on a prediction. A system according to invention principles addresses these deficiencies and related problems.

SUMMARY OF THE INVENTION

A system varies characteristics of an angiographic X-ray imaging acquisition automatically by establishing rules determining acquisition characteristics based on content of previously acquired images. An Angiographic X-ray imaging system includes a detector for automatically detecting a transition between different phases of contrast enhanced blood flow in vessels of a portion of patient anatomy, in response to pixel luminance content of at least one image of a sequence of acquired images of the portion of patient anatomy. A repository of information associates multiple different sets of X-ray imaging device settings with corresponding multiple different phases of contrast enhanced blood flow in vessels including a first set of settings associated with a first phase and a different second set of settings associated with a different second phase. An individual set of X-ray imaging device settings includes at least one of, (a) a radiation dose setting and (b) an image acquisition frame rate. An X-ray imaging device uses the detector and the information for automatically adaptively acquiring a sequence of images of the portion of patient anatomy by sequentially acquiring at least one image in the first phase using the first set of settings and at least one image in the second phase using the second set of settings, in response to detection of a transition between the first and second phases.

DETAILED DESCRIPTION OF THE INVENTION

A system according to invention principles acquires images in multiple different phases individually having a corresponding acquisition frame rate and X-ray radiation dose using a set of triggers. A set of triggers is predetermined to identify different phases of an image acquisition comprising, initial detection of contrast presence, detection of contrast presence higher than a threshold, and detection of a reduction in contrast presence from a detected peak. The system employs known image analysis methods including maximum or minimum luminance detection of image features comprising multiple pixels, edge detection of substantially contiguous image portions comprising multiple pixels based on change in luminance exceeding a threshold and other known method for example, to determine different phases of an image acquisition. The system varies characteristics of an angiographic X-ray imaging acquisition automatically by establishing rules determining acquisition characteristics based on content of previously acquired images.

Figure 1:
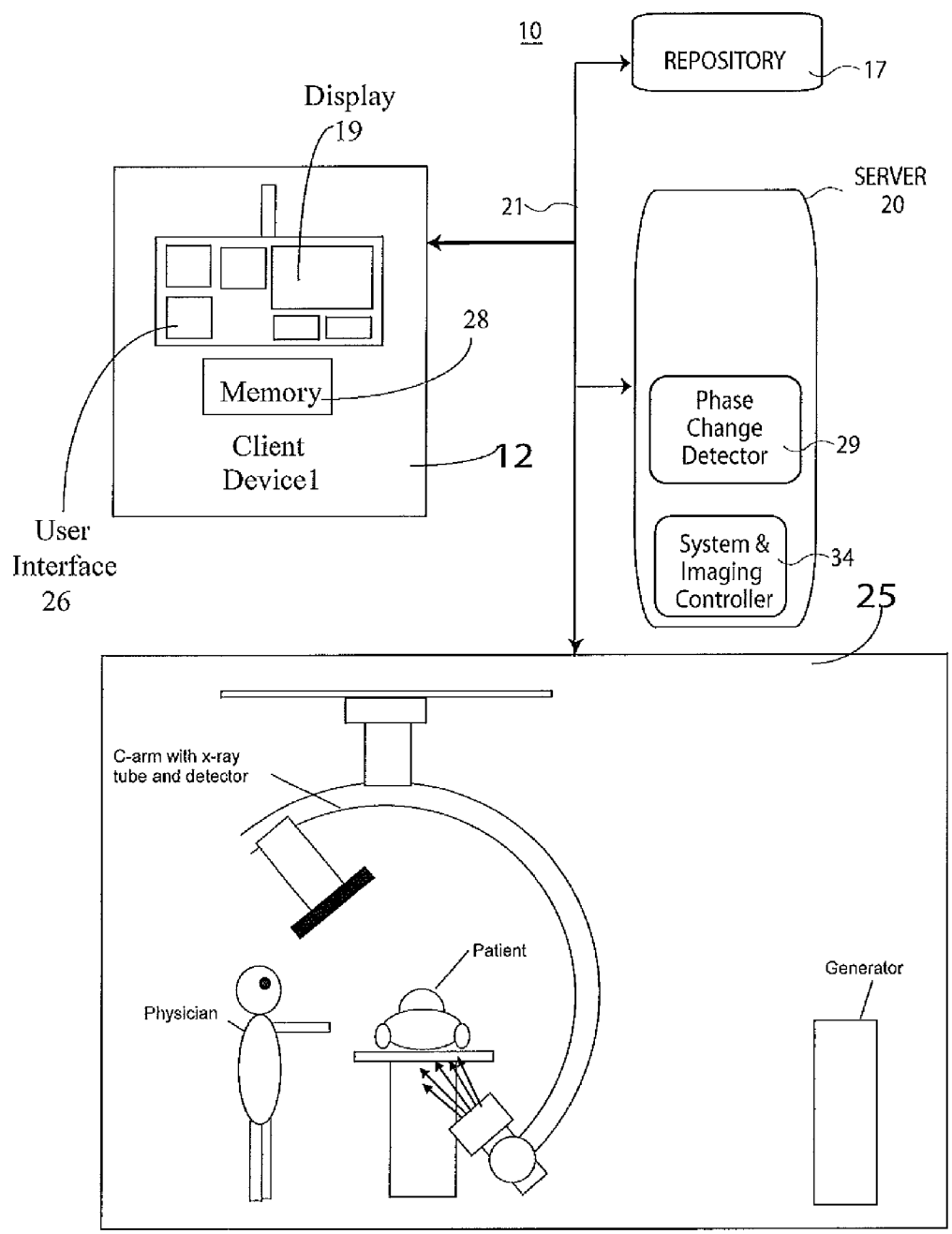
FIG. 1 shows an Angiographic X-ray imaging system, according to invention principles.

FIG. 1 shows an Angiographic X-ray imaging system 10. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. X-ray modality system 25 comprises a C-arm X-ray radiation source and detector device rotating about a patient table and an associated electrical generator for providing electrical power for the X-ray radiation system. The display images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images. Server 20 includes phase change detector 29 and system and imaging controller 34. Display 19 presents display images comprising a Graphical User Interface (GUI). Imaging controller 34 controls operation of imaging device 25 in response to user commands entered via user interface 26. In alternative arrangements, one or more of the units in server 20 may be located in device 12 or in another device connected to network 21.

Phase change detector 29 automatically detects a transition between different phases of contrast enhanced blood flow in vessels of a portion of patient anatomy, in response to pixel luminance content of at least one image of a sequence of images of the portion of patient anatomy acquired using X-ray imaging device 25. Repository 17 of information associates multiple different sets of X-ray imaging device settings with corresponding multiple different phases of contrast enhanced blood flow in vessels including a first set of settings associated with a first phase and a different second set of settings associated with a different second phase. An individual set of X-ray imaging device settings includes at least one of, (a) a radiation dose setting and (b) an image acquisition frame rate, X-ray imaging system 10 uses detector 29 and the information for automatically adaptively acquiring a sequence of images of the portion of patient anatomy by sequentially acquiring at least one image in the first phase using the first set of settings and at least one image in the second phase using the second set of settings, in response to detection of a transition between the first and second phases.

Figure 2:
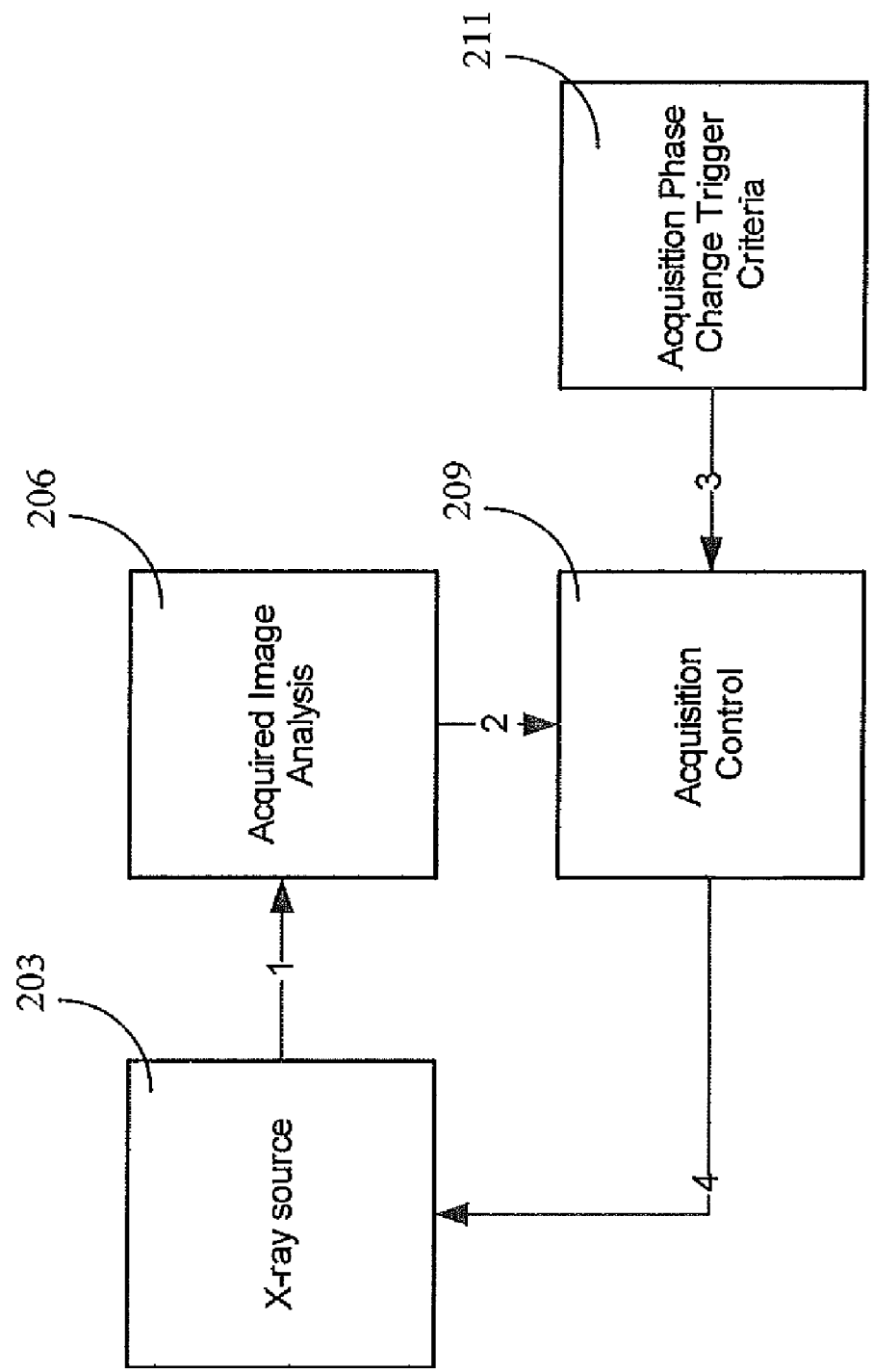
FIG. 2 shows control signal flow for controlling X-ray image acquisition attributes based on image content, according to invention principles.

FIG. 2 shows control signal flow and structure for controlling X-ray image acquisition attributes based on image content. X-ray source 203 sends an image (1) to acquisition system 206 which analyzes the image to identify values of a predetermined set of attributes and sends the attribute values (2) to acquisition control system 209. Acquisition control system 209 uses a table of acquisition phase change trigger criteria (3) derived from trigger criteria repository 211 to determine if the image attribute values (2) result in an acquisition phase change. If a phase change is indicated, X-ray source 203 is updated (4) with the new X-ray parameters (including frame rate and radiation dose).

Figure 3:
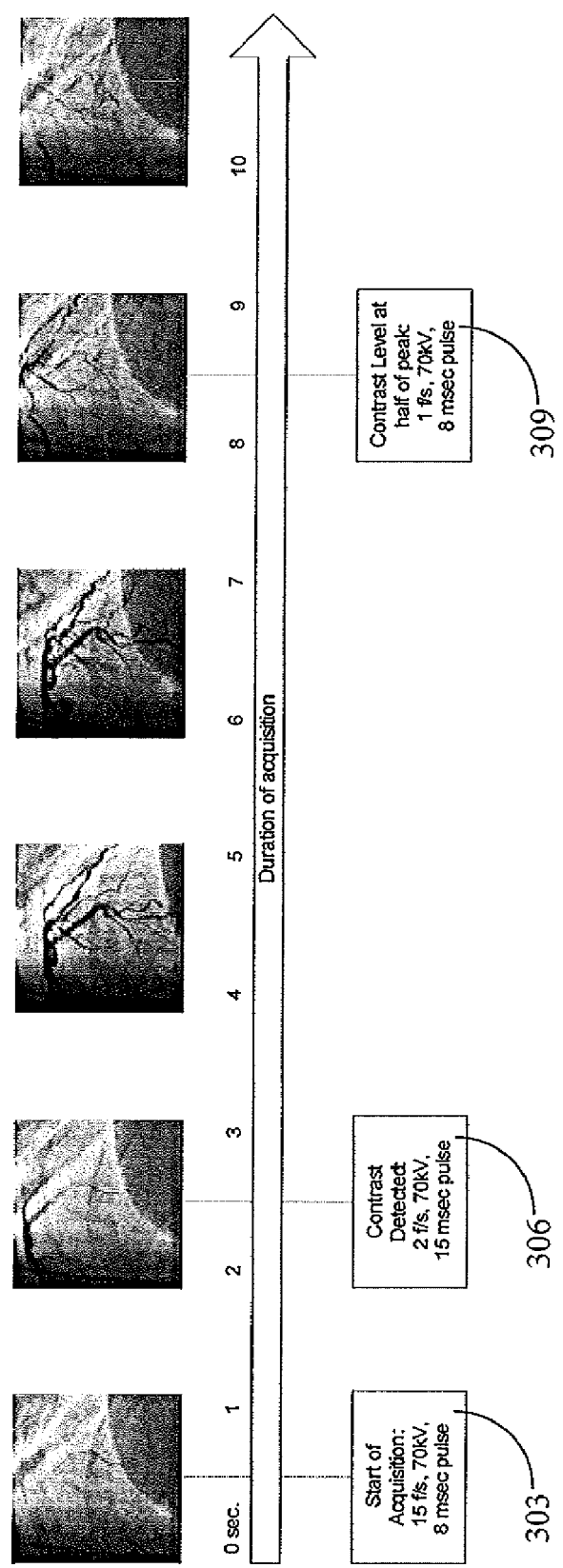
FIG. 3 shows a timeline of a sample image sequence acquisition including image-based phase change, according to invention principles.

FIG. 3 shows a timeline of a sample image sequence acquisition including image-based phase change. Imaging device 25 (FIG. 1) initiates image acquisition at step 303 at 15 frames per second (f/s) with exposure settings of 70 kV and an 8 msec X-ray pulse per frame. After 2 seconds in step 306, a contrast injection is detected by detector 29, and in response controller 34 changes the imaging device 25 acquisition frame rate to 3 f/s with exposure settings of 70 kV and a 15 msec X-ray pulse. After an additional 6 seconds in step 309, the contrast level is determined by detector 29 to be half that of the peak, and the acquisition frame rate of imaging device 25 is changed to 1 f/s with an 8 msec pulse by controller 34.

In a further embodiment, phase change detector 29 detects a specific device in an image such as a stent or balloon catheter based on image analysis and using stored template shape data enabling mapping of a detected object outline to a predetermined outline of a known object. An object outline is determined using an edge detection method involving detecting a substantially continuous line showing a transition in pixel luminance. A detector automatically detects a transition from one phase to another as a result of a specific device being detected in the image, such as a transition from a non-inflated to an inflated balloon catheter. An X-ray imaging device uses the detector and transition information for automatically adaptively acquiring a sequence of images of a portion of patient anatomy including the inflated and non-inflated balloon catheter by sequentially acquiring at least one image in a first phase of the non-inflated balloon using a first set of settings and at least one image in a second phase of the inflated balloon using a second set of settings, in response to detection of a transition between the first and second phases. The characteristics of the balloon are known before the acquisition to facilitate balloon detection in the images as they are acquired.

In another embodiment detector 29 automatically detects a gross image content change. For example, during an image sequence acquisition, a gross change in the image content is detected and causes a change in X-ray parameters, such as a frame rate increase and radiation dosage change that allows movement to be visualized easier. Similarly, detection of a stable image causes another transition involving slowing frame rate down since there is less motion to track. In other embodiments image resolution, field of view, collimation, filters are adaptively changed in response to transition detection. Another type of transition comprises scanning different portions of anatomy requiring different imaging characteristics.

Figure 4:
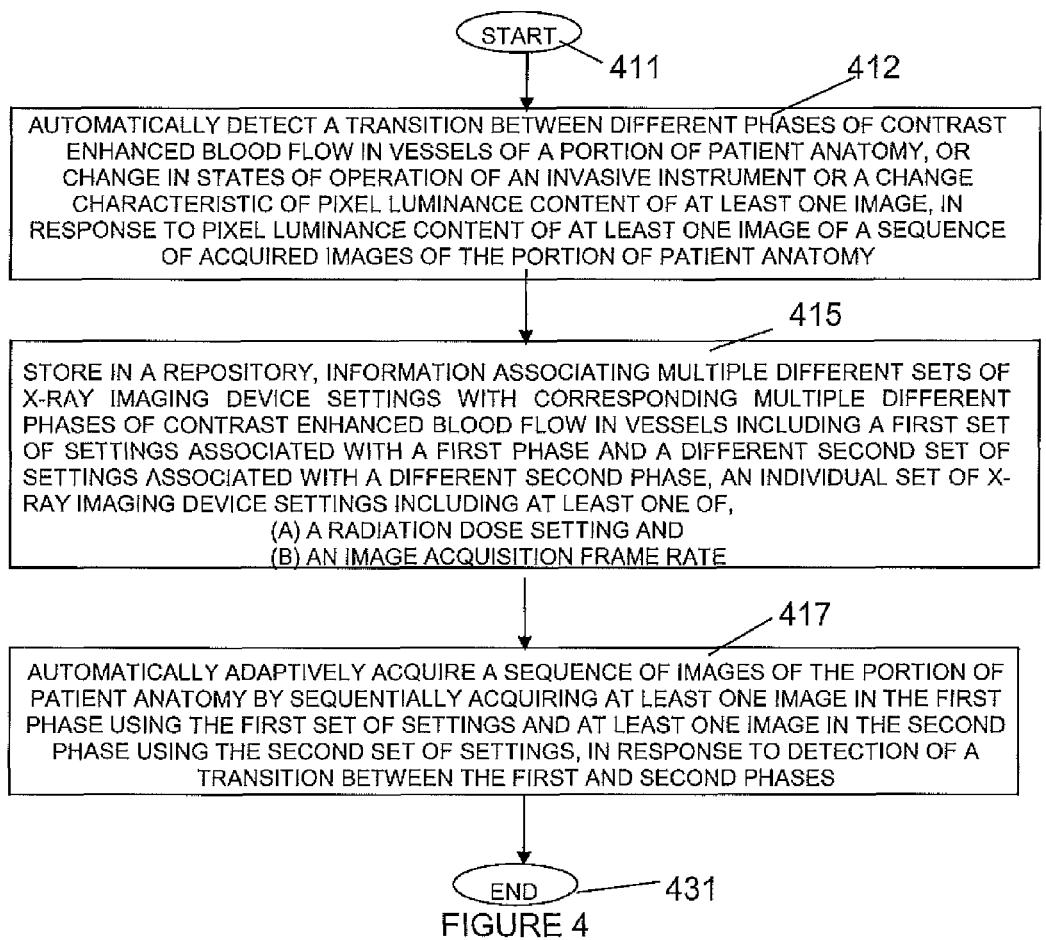
FIG. 4 shows a flowchart of a process used by an Angiographic X-ray imaging system, according to invention principles.

FIG. 4 shows a flowchart of a process used by Angiographic X-ray imaging system 10. In step 412 following the start at step 411, phase change detector 29 automatically detects a transition between different phases of contrast enhanced blood flow in vessels of a portion of patient anatomy, in response to pixel luminance content of at least one image of a sequence of acquired images of the portion of patient anatomy. In another embodiment, in step 412 detector 29 automatically detects a transition between different states of operation of an invasive instrument in a portion of patient anatomy, in response to pixel luminance content of at least one image of a sequence of acquired images of the portion of patient anatomy. The invasive instrument comprises a balloon catheter and the different states of operation of the balloon catheter comprise an inflated state and a non-inflated state, for example. In a further embodiment, in step 412, detector 29 automatically detects a change characteristic of pixel luminance content of at least one image of a sequence of acquired images of the portion of patient anatomy, the change characteristic comprising a change between successive images at least one of, (a) exceeding and (b) being below, a predetermined amount over a predetermined minimum area of an image.

In step 415, controller 34 stores in repository 17, information associating multiple different sets of X-ray imaging device settings with corresponding multiple different phases of contrast enhanced blood flow in vessels including a first set of settings associated with a first phase and a different second set of settings associated with a different second phase. An individual set of X-ray imaging device settings includes at least one of, (a) a radiation dose setting, (b) an image acquisition frame rate (c) an image resolution setting, (d) a field of view setting, (e) a collimator setting and (f) an X-ray filter setting. The radiation dose setting comprises at least one of, an acceleration voltage and an X-ray radiation exposure pulse width. The different phases of contrast enhanced blood flow in vessels comprise at least two of, (a) a phase prior to detection of contrast agent in the vessels in an imaging sequence, (b) a phase following detection of contrast agent in the vessels in an imaging sequence, (c) a phase during which detected contrast agent exceeds a predetermined threshold in the vessels in an imaging sequence and (d) a phase following a detected peak in contrast agent in the vessels in an imaging sequence.

In step 417, X-ray imaging device 25 automatically adaptively acquires a sequence of images of the portion of patient anatomy (or of an invasive instrument) by sequentially acquiring at least one image in the first phase using the first set of settings and at least one image in the second phase using the second set of settings, in response to detection of a transition between the first and second phases or in another embodiment in response to detection of the change in pixel luminance content of at least one image. X-ray imaging device 25 uses the detector and the information for automatically adaptively acquiring a sequence of images of the portion of patient anatomy by sequentially acquiring at least one image in a third phase using a third set of settings, in response to detection of a transition between the second phase and the third phase. In another embodiment, in step 417, X-ray imaging device 25 uses the detector and the information for automatically adaptively acquiring a sequence of images of the invasive instrument by sequentially acquiring at least one image in a first state using the first set of settings and at least one image in a second state using the second set of settings, in response to detection of a transition between the first and second states. The process of FIG. 4 terminates at step 431.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system acquires image in multiple different phases individually having a corresponding acquisition frame rate and X-ray radiation dose using a set of triggers associated with level of contrast agent presence in an image identified using known image analysis methods. Further, the processes and applications may, in alternative embodiments, be located on one or more (e.g., distributed) processing devices on a network linking the units of FIG. 1. Any of the functions and steps provided in FIGS. 1-4 may be implemented in hardware, software or a combination of both.

What is claimed is:

1. An Angiographic X-ray imaging system, comprising:
   a detector for,
      automatically detecting a peak in contrast agent enhanced blood flow and a transition between different phases of contrast agent enhanced blood flow in vessels of a portion of patient anatomy, in response to pixel luminance content of at least one image of a sequence of acquired images of the portion of patient anatomy;
      automatically detecting a transition between different states of operation of an invasive instrument in a portion of patient anatomy, in response to a transition in pixel luminance content of at least one image of said sequence of acquired images of the portion of patient anatomy;
   a repository of information associating a plurality of different sets of X-ray imaging device settings with a corresponding plurality of different phases of contrast agent enhanced blood flow in vessels including a first set of settings associated with a first phase and a different second set of settings associated with a different second phase, an individual set of X-ray imaging device settings including an X-ray radiation exposure pulse width and at least one of,
      (a) a radiation dose setting and
      (b) an image acquisition frame rate; and
   an X-ray imaging device for using said detector and said information for automatically adaptively acquiring a sequence of images of said portion of patient anatomy including said invasive instrument in a particular state by sequentially acquiring at least one image in said first phase using said first set of settings and at least one image in said second phase using said second set of settings, in response to detection of a transition between the first and second phases.

2. A system according to claim 1, wherein
   the different phases of contrast agent enhanced blood flow in vessels comprise, (a) a phase during which detected contrast agent exceeds a predetermined threshold in said vessels in an imaging sequence and (b) a phase following a detected peak in contrast agent in said vessels in an imaging sequence and
   said detector automatically detects in said sequence of images, said invasive instrument in a first state and in a different second state.

3. A system according to claim 1, wherein
   said radiation dose setting comprises an acceleration voltage and
   said detector detects a peak in contrast agent enhanced blood flow and a phase following the detected peak in contrast agent flow in said vessels in an imaging sequence.

4. A system according to claim 1, wherein
   said detector detects a peak in contrast agent enhanced blood flow and a phase following the detected peak in contrast agent in said vessels in an imaging sequence and a phase during which detected contrast agent exceeds a predetermined threshold in said vessels in an imaging sequence.

5. A system according to claim 1, wherein said X-ray imaging device uses said detector and said information for automatically detecting a third phase and adaptively acquiring a sequence of images of said portion of patient anatomy by sequentially acquiring at least one image in said third phase using a third set of settings, in response to detection of a transition between said second phase and said third phase.

6. A system according to claim 1, wherein said X-ray imaging device settings include an image resolution setting.

7. A system according to claim 1, wherein said X-ray imaging device settings include at least one of,
(i) a collimator setting and
(ii) an X-ray filter setting.

8. An Angiographic X-ray imaging system, comprising:
a detector for,
automatically detecting a peak in contrast agent enhanced blood flow and a phase following the detected peak in contrast agent flow and a transition between different states of operation of an invasive instrument in a portion of patient anatomy, in response to pixel luminance content of at least one image of a sequence of acquired images of the portion of patient anatomy;
automatically detecting a transition between different states of operation of an invasive instrument in a portion of patient anatomy, in response to a transition in pixel luminance content of at least one image of said sequence of acquired images of the portion of patient anatomy;
a repository of information associating a plurality of different sets of X-ray imaging device settings with a corresponding plurality of different states of operation of an invasive instrument including a first set of settings associated with a first state and a different second set of settings associated with a different second state, an individual set of X-ray imaging device settings including an X-ray radiation exposure pulse width and at least one of,
(a) a radiation dose setting and
(b) an image acquisition frame rate; and
an X-ray imaging device for using said detector and said information for automatically adaptively acquiring a sequence of images of said invasive instrument by sequentially acquiring at least one image in said first state using said first set of settings and at least one image in said second state using said second set of settings, in response to detection of a transition between the first and second states in said phase following the detected peak in contrast agent flow.

9. A system according to claim 8, wherein said invasive instrument comprises a balloon catheter and said detector automatically detects in said sequence of images, at least one image in said first phase and at least one image in said second phase.

10. A system according to claim 9, wherein said different states of operation of said balloon catheter comprise an inflated state and a non-inflated state.

11. A system according to claim 8, wherein said radiation dose setting comprises an acceleration voltage.

12. A system according to claim 8, wherein said detector detects a phase during which detected contrast agent exceeds a predetermined threshold in said vessels in an imaging sequence.

13. A method for Angiographic X-ray imaging, comprising the activities of:
automatically detecting a peak in contrast agent enhanced blood flow and a phase following the detected peak in contrast agent flow, in response to pixel luminance content of at least one image of a sequence of acquired images of the portion of patient anatomy;
automatically detecting a transition between different states of operation of an invasive instrument in a portion of patient anatomy, in response to a transition in pixel luminance content of at least one image of said sequence of acquired images of the portion of patient anatomy;
storing in a repository, information associating a plurality of different sets of X-ray imaging device settings with a corresponding plurality of different phases of contrast agent enhanced blood flow in vessels including a first set of settings associated with a first phase and a different second set of settings associated with a different second phase, an individual set of X-ray imaging device settings including an X-ray radiation exposure pulse width and at least one of,
(a) a radiation dose setting and
(b) an image acquisition frame rate; and
automatically adaptively acquiring a sequence of images of said portion of patient anatomy including said invasive instrument in a particular state by sequentially acquiring at least one image in said first phase using said first set of settings and at least one image in said second phase using said second set of settings, in response to detection of a transition between the first and second phases.

14. A method according to claim 13, wherein the different phases of contrast agent enhanced blood flow in vessels comprise at least two of, (a) a phase prior to detection of contrast agent in said vessels in an imaging sequence, (b) a phase following detection of contrast agent in said vessels in an imaging sequence, (c) a phase during which detected contrast agent exceeds a predetermined threshold in said vessels in an imaging sequence and (d) a phase following a detected peak in contrast agent in said vessels in an imaging sequence and including the activity of
automatically detecting in said sequence of images, said invasive instrument in a first state and in a different second state.

15. A method according to claim 13, wherein said X-ray imaging device settings include at least one of,
(i) an image resolution setting and
(ii) a field of view setting.

16. A method according to claim 13, wherein said X-ray imaging device settings include at least one of,
(i) a collimator setting and
(ii) an X-ray filter setting.

17. A method for Angiographic X-ray imaging, comprising the activities of:
automatically detecting a peak in contrast agent enhanced blood flow and a phase following the detected peak in contrast agent flow and a change characteristic of pixel luminance content of at least one image of a sequence of acquired images of the portion of patient anatomy, said change characteristic comprising a change between successive images at least one of, (a) exceeding and (b) being below, a predetermined amount over a predetermined minimum area of an image;

automatically detecting a transition between different states of operation of an invasive instrument in a portion of patient anatomy, in response to a transition in pixel luminance content of at least one image of said sequence of acquired images of the portion of patient anatomy;

storing in a repository, information associating a plurality of different sets of X-ray imaging device settings with a corresponding plurality of different phases of contrast agent enhanced blood flow in vessels including a first set of settings associated with a first phase and a different second set of settings associated with a different second phase, an individual set of X-ray imaging device settings including at least one of, (a) a radiation dose setting and (b) an image acquisition frame rate; and automatically adaptively acquiring a sequence of images of said portion of patient anatomy including said invasive instrument in a particular state by sequentially acquiring at least one image in said first phase using said first set of settings and at least one image in said second phase using said second set of settings, in response to detection of said change in pixel luminance content of at least one image.

18. A method according to claim 17, wherein
said X-ray imaging device settings include at least one of,
(i) an image resolution setting and
(ii) a field of view setting and including the activity of
automatically detecting in said sequence of images, said invasive instrument in a first state and in a different second state.

19. A method according to claim 17, wherein
said X-ray imaging device settings include at least one of,
(i) a collimator setting and
(ii) an X-ray filter setting.

20. A method according to claim 19, wherein
said X-ray imaging device settings include at least one of,
(i) an image resolution setting and
(ii) a field of view setting.

21. A method according to claim 17, wherein
said X-ray imaging device settings include an X-ray radiation exposure pulse width.

\* \* \* \* \*